US012551628B2

(12) United States Patent
Etter et al.

(10) Patent No.: US 12,551,628 B2
(45) Date of Patent: Feb. 17, 2026

(54) ELECTRONIC MODULE FOR MEDICAMENT DELIVERY DEVICE

(71) Applicant: Ypsomed AG, Burgdorf (CH)

(72) Inventors: Leoni Etter, Bern (CH); Manuel Hulliger, Gerlafingen (CH); Stefan Mangold, Liebefeld (CH); Dominik Zumstein, Lyss (CH); Simon Martin Bosshard, Hindelbank (CH); Christian Schrul, Oberburg (CH)

(73) Assignee: Ypsomed AG, Burgdorf (CH)

( * ) Notice: Subject to any disclaimer, the term of this patent is extended or adjusted under 35 U.S.C. 154(b) by 0 days.

(21) Appl. No.: 19/334,364

(22) Filed: Sep. 19, 2025

(65) Prior Publication Data

US 2026/0021254 A1 Jan. 22, 2026

Related U.S. Application Data

(63) Continuation of application No. PCT/EP2024/055700, filed on Mar. 5, 2024.

(30) Foreign Application Priority Data

Mar. 27, 2023 (EP) .................................... 23164208

(51) Int. Cl.
*A61M 5/20* (2006.01)
*A61M 5/315* (2006.01)

(52) U.S. Cl.
CPC .... *A61M 5/31568* (2013.01); *A61M 5/31525* (2013.01); *A61M 2005/2006* (2013.01); (Continued)

(58) Field of Classification Search
CPC ............ A61M 5/20; A61M 2005/2013; A61M 5/2033; A61M 5/31568; A61M 5/31525; (Continued)

(56) References Cited

U.S. PATENT DOCUMENTS

2014/0243749 A1 8/2014 Edwards et al.
2016/0287788 A1 10/2016 Tremblay et al.
(Continued)

FOREIGN PATENT DOCUMENTS

EP 4122512 A1 1/2023
EP 4438083 A1 10/2024
(Continued)

OTHER PUBLICATIONS

Extended European Search Report issued in European Patent Application No. 23164208.3, mailed on Sep. 15, 2023, 7 pages.
(Continued)

*Primary Examiner* — Michael J Tsai
*Assistant Examiner* — Benjamin Koo
(74) *Attorney, Agent, or Firm* — Dorsey & Whitney LLP

(57) ABSTRACT

An electronic module configured for releasable attachment to a medicament delivery device (20) includes a printed circuit board (16*c*) with an electronic circuit (29), a battery (16*b*), and a switch for activating the electronic module (16). The switch includes an electric activation contact (28) providing a connection with the electronic circuit (29) and a battery contact extension (27) extending from a terminal (16*d*, 16*e*) of the battery (16*b*). The battery contact extension (27) is biased towards the electric contact (28) for closing a switching or air gap (30) between the battery contact extension (27) and the electric activation contact (28), and the battery contact extension (27) is configured to engage an actuation element (11, 6) of the medicament delivery device (20) such that the actuation element (11, 6) pushes the battery contact extension (27) against the bias thereby creating the switching or air gap (30).

17 Claims, 6 Drawing Sheets

(52) U.S. Cl.
CPC ............... *A61M 2205/3561* (2013.01); *A61M 2205/8206* (2013.01)

(58) Field of Classification Search
CPC .. A61M 2005/2006; A61M 2205/3561; A61M 2205/8206
See application file for complete search history.

(56) References Cited

U.S. PATENT DOCUMENTS

| | | | | |
|---|---|---|---|---|
| 2017/0192777 | A1 | 7/2017 | Apte et al. | |
| 2018/0243511 | A1* | 8/2018 | Gylleby | A61M 5/3157 |
| 2020/0179612 | A1 | 6/2020 | Wei | |
| 2021/0128841 | A1* | 5/2021 | Andersen | A61M 5/31515 |
| 2021/0196891 | A1 | 7/2021 | Säll et al. | |
| 2022/0288325 | A1* | 9/2022 | Yao | A61M 5/3202 |
| 2022/0401657 | A1 | 12/2022 | Krulevitch et al. | |
| 2024/0358935 | A1* | 10/2024 | Maréchal | A61M 5/31511 |

FOREIGN PATENT DOCUMENTS

| | | | |
|---|---|---|---|
| WO | 2017032586 | A1 | 3/2017 |
| WO | 2023275273 | A1 | 1/2023 |
| WO | 2024199911 | A1 | 10/2024 |

OTHER PUBLICATIONS

International Search Report and Written Opinion issued in International Application No. PCT/EP2024/055700, mailed on Aug. 9, 2024, 12 pages.

Third Party Observation filed into International Application No. PCT/EP2024/055700, filed on Mar. 5, 2024, 24 pages.

* cited by examiner

Prior Art

ELECTRONIC MODULE FOR MEDICAMENT DELIVERY DEVICE

CROSS REFERENCE TO RELATED APPLICATIONS

This application claims priority to International Patent Application No. PCT/EP2024/055700, filed Mar. 5, 2024, entitled "ELECTRONIC MODULE FOR MEDICAMENT DELIVERY DEVICE," which in turn claims priority to European Patent Application No. 23164208.3, filed Mar. 27, 2023, entitled "ELECTRONIC MODULE FOR MEDICAMENT DELIVERY DEVICE", each of which is incorporated by reference herein, in the entirety and for all purposes.

TECHNICAL FIELD

Provided is an electronic module for a medicament delivery device including a switch for activating the electronic module.

BACKGROUND

Injection or infusion devices such as injections pens, auto injectors, autopens, patch injectors or patch pumps, use a drive mechanism for expelling medicament from the device. The drive mechanism includes mechanical components for advancing, for example, a piston rod forwarding a stopper or piston head in a reservoir or to drive a pumping mechanism. The injection or infusion devices may be disposable or reusable devices. These devices are mainly mechanically driven using springs or are driven by gas that is either generated in-situ or compressed in a cartridge. These mechanical devices have features for providing feedback to the user such as a start of injection click, or an end of injection click generated by the drive mechanism. The monitoring functions of these devices for providing feedback to the user are limited by the mechanical drive mechanism used.

In EP 4122512 A1 an autoinjector is disclosed with a module housing closing an electronic module that is releasable attached to a main housing including the injection mechanism. The electronic module includes a separate switch attached to a printed circuit board (PCB) for actuating the module thereby requiring additional components that consume space in the module.

WO 2017032586 presents a monitoring unit for a medicament delivery device with an actuation switch. The actuation switch is a separate switch positioned on the PCB thereby requiring additional components and additional length of the monitoring unit.

US 2021/0196891 A1 discloses a medicament delivery device housing a monitoring unit powered by a battery and being designed to be activated upon dose delivery. The activation being effectuated by an insulating part wedged between the battery and a terminal contact, designed to be pulled away by being operably connected to an actuation member that is axially moved during dose delivery, resulting in closure of the electronic circuit.

US 2014/243749 A1 shows a medicament delivery device with an electronic control unit being powered by a battery. The battery being in contact with a flexible clip extending from the PCB at one end and clamping the battery to the PCB at the other end. The cap of the device features a battery insulating protrusion, which is wedged between the clip and the battery and is removed when the cap is removed, resulting in activation of the control unit.

US 2022/288325 A1 relates to a cap assembly with an electronic control unit of an autoinjector device. The cap is provided with a spiral spring that relaxes upon removing the cap and closes the electronic circuit. The control unit is designed to record dose delivery events by registering removal of the cap.

SUMMARY

In view of the foregoing, there is a need to include additional monitoring and communication features to those mechanical devices for example by adding electronic modules to the mechanical device. Examples for those electronic modules may be a communication module with a transmitter and/or receiver to allow communication with other devices, a sensing module for sensing device or drug delivery states, or patient parameters such as blood glucose values, a location module indicating geographical locations, a timer or calendar module, a communication or training module including a loudspeaker. The electronic module may be added as a separate add-on or supplementary device to the existing mechanically driven device. The add-on may be integrated into the mechanical device by the device manufacturer, as a so-called integrated add-on that may be removed after use.

The electronic module is configured to monitor functions of the device such as, for example, the start of the injection, the end of injection, the holding time after injection, the removal of the electronic module, the re-attachment of the electronic module to another medicament delivery device after being used on a medicament delivery device, monitoring and counting the number of times the monitoring unit has been attached to a plurality of devices (lifetime management), the identification of the medicament used, and the like. The data may be stored in a storage module of the electronic module and the electronic module may be configured to transmit the data to an external device or to receive information from an external device.

The electronic module needs to be powered by a battery and the service lifetime of the module may be restricted by the battery capacity and/or the time that the electronic module is active or at least a part of the electronic module is active. The electronic module may be activated to switch-on the electronic module, or a part of the electronic module may be activated for monitoring functions of the medicament delivery device. The electronic module therefore needs a switch element for activating and/or actuating the electronic module.

It is therefore an object of the present disclosure to address the aforementioned needs by providing an improved electronic module a medicament delivery device including the electronic module, which is or includes a robust and reliable electronic module requiring less components allowing for space saving configurations. These objectives are solved by the claims.

Accordingly, disclosed is an electronic module for a medicament delivery device. The electronic module may include a printed circuit board (PCB), an electronic circuit being located on the printed circuit board, a battery, and a switch element for activating the electronic module. The switch element includes an electric activation contact that is part of and connected to the electronic circuit and a battery contact extension extending from and contacting a terminal of the battery. The battery contact extension is biased towards the electric activation contact for closing a switching gap between the battery contact extension and the electric activation contact. The battery contact extension is configured for engaging an actuation element of the medicament delivery device adapted to compensate the bias of the battery contact extension and to maintain the switch element open in an initial or shipping state of the actuation element, e.g. prior to medicament delivery. The switching gap is a physical or air gap between the battery contact extension and the electric activation contact, devoid of any solid-state insulator.

An electronic module is presented that is configured for releasable attachment to a medicament delivery device including a printed circuit board with an electronic circuit, a battery and an activation contact providing a connection to the electronic circuit. A battery contact extension extends from a terminal of the battery, the battery contact extension is biased towards the activation contact for closing a switching gap between the battery contact extension and the electric activation contact. The battery contact extension is configured to engage an actuation element of the medicament delivery device such that the actuation element may force the battery contact extension against the bias in or into an open state of the switch element.

The electronic module may be configured for releasable attachment to and subsequent detachment from the medicament delivery device. The electronic module may be releasable attached to the same or another medicament delivery device. The same medicament delivery device and the another medicament delivery may include the same delivery mechanism or same mechanical interface for connecting the electronic module. The medicament delivery device may be an injection device, an auto injector, or a patch injector.

The printed circuit board may be rigid, flexible or include flexible and rigid elements. The combination of rigid and flexible elements may allow for stacking of the rigid PCB elements on top of each other for a space saving configuration of the PCB in the electronic module. The battery may be rechargeable or non-rechargeable for powering the electronic module. The battery may be connected to the PCB and may be provided in a battery holder. The battery holder may be mechanically connected to the PCB or may be fixated to a part of the housing of the electronic module, for example to a closure cap or housing of the electronic module. Further components of the electronic module that may be located on the PCB include a microprocessor, a transmitter, a receiver, an antenna, a storage module, a communication module for the user or a scanner or camera. The communication module may include a visual display such as an LCD or OLED display, a loudspeaker, or buzzer. The scanner may be configured to read bar codes or 2-dimensional QR codes. The electronic module may include an input device such as a touch sensitive screen.

The actuation of the switch element may activate or wake up the electronic module or activate the microprocessor located on the PCB. Actuation of the switch element may also de-activate the electronic circuit or de-activate a part of the electronic circuit.

The switch element includes an electric activation contact or contact area on, or part of the electronic circuit. One end of the battery contact extension contacts the terminal of the battery or contacts a battery holder holding the battery. The battery contact extension may also be part of, or extend from the battery holder holding and contacting the battery. The battery contact extension is biased towards the electric activation contact or contact area and configured to close the switching gap between the battery contact extension and the electric activation contact and close the switch element. The battery contact extension is configured to engage the actuation element of the medicament delivery device which may be a drive element or a signaling element or a display element. The actuation element of the medicament delivery device is configured to force, or axially displace at least a part of the battery contact extension against the bias thereby configured to create the switching gap and opening the switch element. The switch element is open or not actuated. Compared to the prior art, an additional switch and activation element of the medicament delivery device may not be required such that the electronic module can be actuated with less components and represents a space saving configuration. The space may be used, for example, for a battery with a larger capacity.

Upon detachment or removal of the electronic module from the medicament delivery device, the switch element may be actuated as there is no engagement between the actuation element and the battery contact extension and the bias on the battery contact extension closes the switch element.

When the electronic module is attached to the medicament delivery device then the switch element may be actuated by the delivery mechanism of the medicament delivery device. The switch element may be actuated several times and each time the activation of the switch element may trigger a signal different from the previously generated signal by the electronic module. The switch element may be actuated upon attachment of the module or may be actuated when the medicament delivery device is used during medicament delivery or may be actuated when the electronic module is removed. The switch element may monitor several functions or states of the medicament delivery device throughout its service life.

The electronic circuit or the microprocessor in the electronic circuit or the receiver/transmitter may be activated by the switch element when the switching gap is closed for a defined minimum closure time. Wake up of the electronic circuit may be established when the contact is established (switch element is closed) for a certain duration, for example more than 10 milliseconds, or more than 100 milliseconds. Closing the switch element may initially start the wake-up procedure for the microprocessor but if not followed by a continued actuation of the switch element, then the electronic module may go back in the sleeping mode. This may avoid unintended actuation, for example during impact (drop-test) where the impact results in a short closure time of the switch element.

The terminals of the battery may be both in permanent contact with the PCB thereby powering the electronic module or powering a part of the electronic circuit permanently. Another part of the electronic circuit may remain in a sleeping mode. The part of the electronic circuit containing power consuming components such as the microprocessor, or the transmitter may initially not be powered by the battery. Actuation of the switch element may act as a load switch thereby adding and powering further components of the electronic circuit. Alternatively, one of the terminals of the battery may be in contact with the PCB and the other terminal may be connected to the PCB via the switch element, in this case the electric power is not supplied to the electronic circuit until the switch element is operated thereby activating the electronic module.

The connectors between the terminals of the battery and the PCB may have a combined electrical (conductive) function and also provide mechanical support to position the battery or the battery holder on the PCB.

The battery contact extension of the electronic module may include a spring element or spring biasing the battery contact extension towards the electric activation contact.

The spring element or spring may be a coil spring, a torsional spring, or a leaf spring. The spring may be attached to, or may be part of the battery holder.

The battery contact extension may include a detection pin and the spring element or spring is located between the terminal of the battery and the detection pin. The spring may also be located between the battery holder and the detection pin. The detection pin may be at the distal end of the battery contact extension and may extend from the spring element.

The actuation element of the medicament delivery device may be configured to abut the detection pin or the distal end of the detection pin of the battery contact extension when the electronic module is attached to or integrated in the medicament delivery device thereby creating the switching gap or opening the switch element. The actuation element of the delivery device and the detection pin of the electronic module may move axially along a longitudinal axis of the delivery device when the actuation element leaves the initial or shipping state during medicament delivery.

The detection pin and the spring element may be provided as a unitary component and made from an electrically conductive material such as a metal. Examples are stainless steel or cupper. The switch element may be configured as a bi-stable clicker element may have two configurations one for the closed switch and one for the open switch. The switch element may be made from a sheet, a wire or is a stamped part. The battery holder, the spring and the detection pin may be made as a unitary component thereby reducing the number of components to be used for the electronic module.

The battery holder holds the battery and contacts the terminals of the battery, and the battery holder may be mechanically fixed to the PCB or to another housing part. The contact between the PCB and the battery or battery holder may provide mechanical support only, or may provide an electric activation contact only or may provide both mechanical support and an electric activation contact.

In embodiments, the spring element is a leaf spring, and the detection pin may extend from the leaf spring and is oriented essentially perpendicular to the leaf spring forming a kink or bend between the leaf spring and the detection pin. Essentially perpendicular is defined as an angle between eighty and one hundred degrees, such as between eighty-five and ninety-five degrees. Alternatively, the detection pin is tilted to the leaf spring with an angle ranging between forty-five and eighty degrees or an angle between one hundred and one hundred forty-five degrees. The spring may be formed by the kink between the leaf spring and the detection pin.

The electric activation contact on the electronic circuit may at least partially surround a passage or boring in the printed circuit board. The electric activation contact may be made from gold or copper and may be integrated in, and connected to the conductive paths of the electronic circuit. The electric activation contact surrounding the passage may be on one side of the PCB. Alternatively, the electric activation contact is on both sides of the PCB.

The detection pin may at least partially pass or go through the passage and the distal end of the detection pin is configured to engage the actuation element of the medicament delivery device. The electric activation contact may advantageously be on one side of the passage and the distal end of the detection pin at the opposite side of the passage.

The kink may be configured for contacting the electric activation contact of the electronic circuit on one side of the passage.

The passage in the PCB may have a fixed dimension, for example a fixed diameter or may have a variable diameter with respect to the central axis of the passage. The passage may be tapered. The distal section of the passage may include a smaller dimension for (mechanically) guiding the detection pin through the passage whereas the proximal part has a greater dimension (diameter) for the electric activation contact. Correct guidance for the battery contact extension may increase the reliability, robustness and impact resistance for the switch. A greater dimension of the entrance section of the passage for receiving the detection pin may be beneficial for reducing the sensitivity of the switch element to tolerance variations during manufacturing.

The PCB may have a plurality of passages, one passage for guidance of the battery contact extension and another passage may provide the electrical switching when closing the switching gap. The battery contact may have a plurality of battery contact extensions.

The kink may be located at one side of the PCB for contacting the electric activation contact and the distal end of the detection pin may be at opposite side of the PCB for contacting the actuation element.

The electric activation contact may at least partially cover the inner surface of the passage. The contact area may be increased from a top surface of the PCB where the electric activation contact at least partially surrounds the passage, to including an inner surface of the passage thereby increasing the reliability of the switch.

The battery contact extension may include a radial or lateral extension and/or a tapered section for contacting the electric activation contact wherein the radial or lateral extension has an outer dimension greater than the inner dimension of the passage. The inner dimension may be the diameter of the passage. The radial or lateral extension may be shaped as a flange. The tapered section may depend from the lateral extension or flange. The radial or lateral extension may be adjacent to the kink and the radial or lateral extension may be positioned between the kink and the tapered section. The radial or lateral extension is configured for contacting the electric activation contact of the electronic circuit surrounding the passage whereas the tapered section is configured for engaging the contact surface inside the passage of the PCB. The tapered section and/or the flange may remove contamination or a corroded surface from the electric activation contact upon closure of the switch. The tapered section may be roughened to act as a sandpaper thereby removing a corrosion layer from the conductive surface that may have built up during shelf life.

The actuation element of the medicament delivery device may axially move along, or tilt with respect to, or rotate around a longitudinal axis of the medicament delivery device when the medicament delivery device is used. When an electronic module is attached to the delivery device, then the actuation element may release the engagement between the actuation element and the battery contact extension and close the switching gap and actuate the switch. The switch element may be repeatedly actuated during use of the medicament delivery device, for example upon attachment of the module to the medicament delivery device or at the start and/or at the end of the injection. When the medicament delivery device is removed after use, the switching gap may be closed again as the actuation element is not in contact with the battery extension. Each time the mechanical actuation of the switch element may activate the electronic module or a part of the electronic module. As an alternative, actuation may de-activate the electronic module or a part of the electronic module.

In another embodiment, the actuation element of the medicament delivery device indirectly actuates the switch element via a coupling part or coupling member which may axially move, tilt or rotate due to the movement of the actuation part during dose delivery and the coupling part or coupling member may abut the battery contact extension, preferably the detection pin.

The electronic module may include a mechanical interface that is configured for releasable attachment to or releasable detachment from a complementary mechanical interface on the medicament delivery device. The mechanical interface includes couplers or coupling means for engaging complementary couplers or coupling means on the complementary mechanical interface of the medicament delivery device. The mechanical interface may be configured for repeated attachment or repeated detachment, or the mechanical interface of the electronic module may only be coupled once to the complementary mechanical interface on the medicament delivery device. The electronic module may, after detachment, not be attached to an (empty) device and may only be attached to a ready to use or full medicament delivery device. This may promote that the therapy may only be started with a full medicament delivery device.

The detection pin of the switch element may be part of or located in the mechanical interface of the electronic module. Alternatively, the switch element is located outside the mechanical interface.

The electronic module described above may be releasably attached to or separatable integrated into a medicament delivery device. The battery contact extension or the detection pin may engage the actuation element of the medicament delivery device during attachment or integration of the electronic module thereby opening the switch element and creating the switching gap against the bias of the spring. The mechanical interface of the electronic module engages a complementary mechanical interface on the medicament delivery device during attachment or integration. The mechanical interface of the electronic module may have arms, elastic arms, protrusions, releasable snap fit connectors, a screw type of connector, a bayonet type connector a push-and-rotate type of connector configured to engage the complementary mechanical interface on the medicament delivery device including recesses rims, elastic arms, screw type of connectors or the counterparts for the bayonet connector or push-and-rotate-type of connectors. The mechanical interface of the electronic module may be configured to lock or unlock the medicament delivery device, e.g., the medicament delivery device may only be operated in an unlocked state with an attached or integrated electronic module.

The medicament delivery device may be a spring driven auto injector including an injection spring for moving a drive element in the distal direction during dose delivery. The injection spring may rotate the actuation element or tilt the actuation element or axially move the actuation element in the distal or delivery direction to release the engagement between the battery contact extension and the actuation element thereby closing the switch. During an injection, the actuation element may move in the proximal direction after first being moved in the distal direction thereby actuating the switch element again.

While the invention has been described in detail in the drawings below and foregoing general description, such description is to be considered illustrative or exemplary and not restrictive. Variations to the disclosed embodiments can be understood and effected by those skilled in the art and practicing the claimed invention, from a study of the drawings, the disclosure, and the appended claims.

DETAILED DESCRIPTION

Definitions

The term "medicament" or "medication" includes any flowable medical formulation suitable for controlled administration through a means such as, for example, a cannula or a hollow needle and includes a liquid, a solution, a gel or a fine suspension containing one or more medical active ingredients. A medicament can be a composition including a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from—or harvested by—biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

The distal end or distal direction is defined by the direction of the hollow needle configured to penetrate the skin of the patient. For an injection device such as an injection pen this may be the injection needle and the end of the pen holding the needle or being configured to hold the needle is the distal end. For an infusion device the distal end and the distal direction is towards the needle configured to penetrate the skin of the patient, which may be along the axis of the device or tilted or perpendicular to the axis of the device. The distal direction in an infusion device represents the direction in which the medicament flows towards the insertion needle. The proximal direction or end is opposite to the distal direction or end.

In the claims, the word "comprising" does not exclude other elements or steps, and the indefinite article "a" or "an" does not exclude a plurality. For example, "a battery extension" does not exclude the fact that there may be two battery extensions that functionally or structurally fulfill the purpose of "a battery extension". The mere fact that certain elements or steps are recited in distinct claims shall not preclude the existence of further meaningful combinations of these elements or steps.

Figure 1:
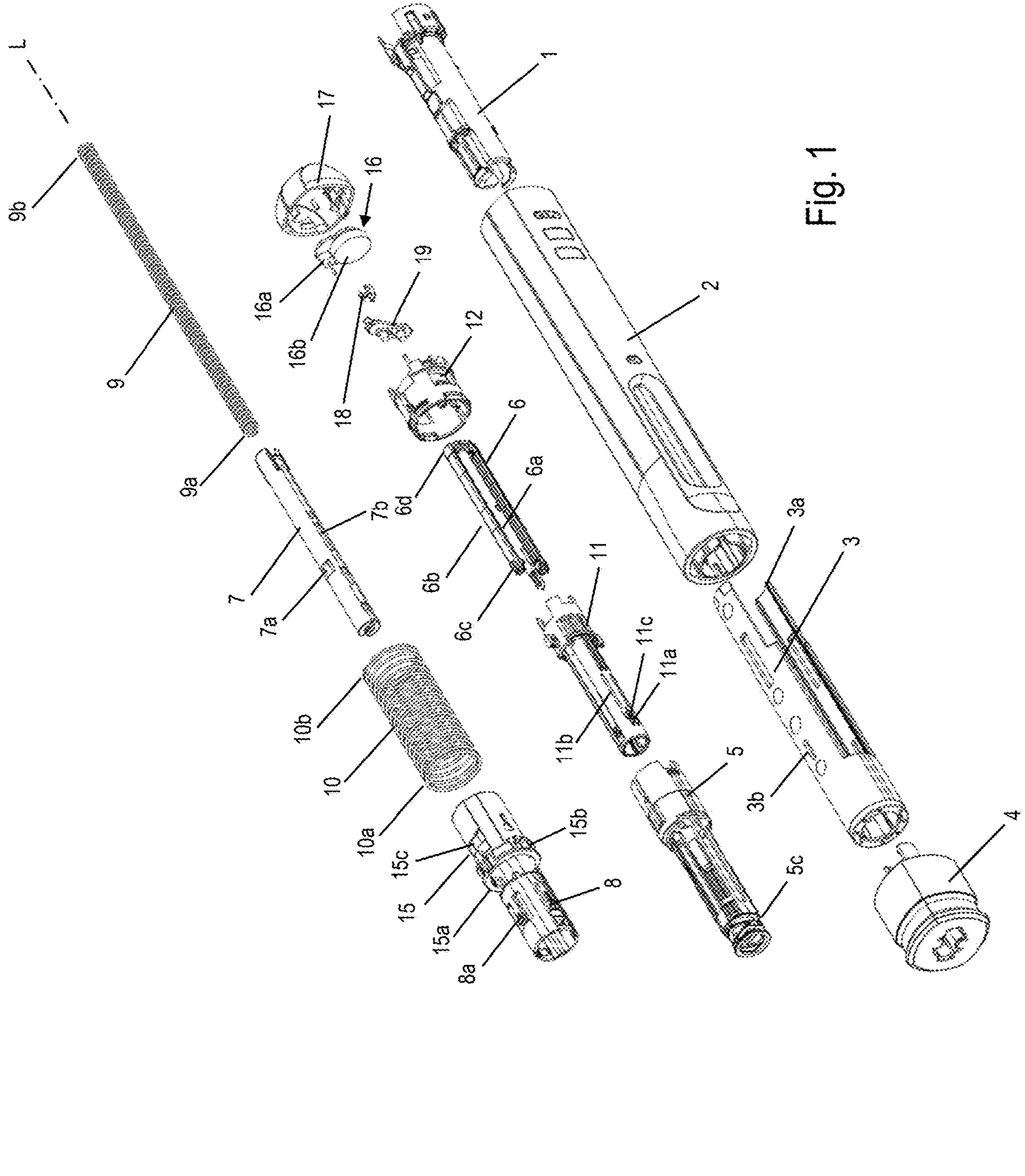
FIG. 1: Exploded view of an autoinjector.
Figure 2A:
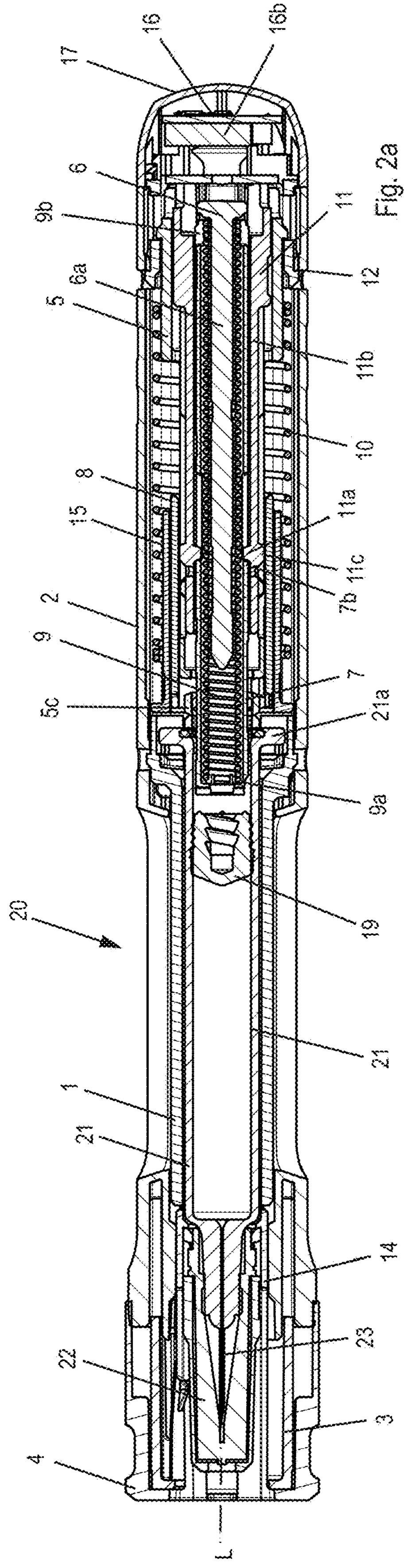
FIG. 2*a*: Longitudinal cross-section of the autoinjector in FIG. 1.
Figure 2B:
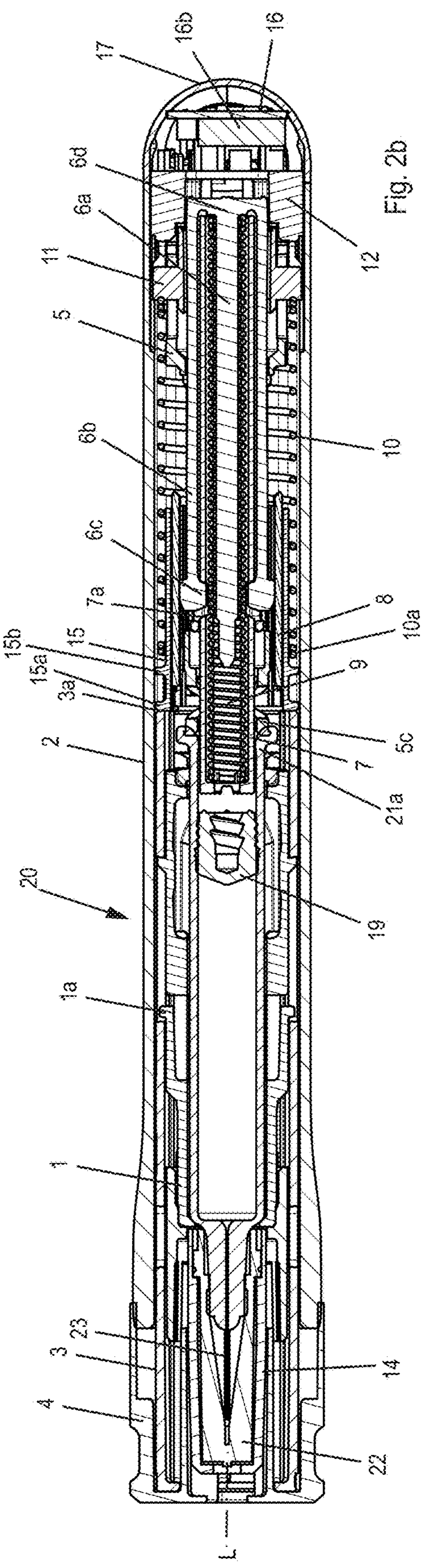
FIG. 2*b*: Longitudinal cross-section of the autoinjector taken perpendicular to the view of FIG. 2*a*, FIG. 3*a*: Longitudinal cross-section of an electronic module according to the prior art with a separate switch and detection pin; autoinjector before use.

Turning to the Figures, FIG. 1 illustrates an exploded view of an autoinjector. An elongated sleeve shaped housing 2 can be gripped by the user during an injection and the housing defines a longitudinal axis L. An injection mechanism that is configured to be driven by a coiled compression spring is enclosed in the housing 2. To illustrate the function of the components, FIGS. 2*a* and 2*b* depict longitudinal sections of the medicament delivery device or autoinjector 20. A prefilled syringe 21 is received in a syringe holder 1 and the syringe holder 1 is axially and rotationally secured to the housing 2 with a snap-fit connection. The autoinjector 20 as delivered to the patient is closed at the distal end by a pen cap 4 that must be removed before using the autoinjector. A needle shield 22 of the prefilled syringe 21 is coupled to the cap 4 by a needle shield remover 14 such that removal of the pen cap 4 also removes the needle shield 22 thereby exposing hollow needle 23. A needle cover sleeve 3 is axially guided by, and can be moved relative to the housing 2 along the longitudinal axis L a distance corresponding to an actuation hub. The needle cover sleeve 3 can slide in the proximal direction for actuating the injection mechanism to expel medicament from the autoinjector 20. A mechanic holder 5 is snap-fitted into and rotationally and axially secured to the housing 2. The mechanic holder 5 includes an elastic element 5*c* (holding spring) at the distal end which abuts the proximal end 21*a* of the prefilled syringe 21 and biases the prefilled syringe distally into the syringe holder 1.

The injection mechanism includes a compression spring acting as an injection spring 9. The injection spring 9 in its initial state is almost completely enclosed by a piston rod 7 and the distal end 9*a* of the injection spring 9 biases the piston rod 7 into the distal direction. The proximal end 9*b* of the injection spring abuts a holding element 6 and the holding element 6 includes two arms 6*b* extending from a proximal end 6*d* in the distal direction and one central pin 6*a* for guiding the injection spring 9. Each arm 6*b* includes a protrusion 6*c* directed towards the axis L and both protrusions engage recesses 7*a* on the outer surface of the piston rod 7. In the initial state of the autoinjector, a switching module 8, 15 including switching sleeve 15 and a locking sleeve 8 prevent a deflection of the arms 6*b* as the arms 6*b* are confined within the locking sleeve 8 and therewith prevent a relative movement between the piston rod 7 and the holding element 6 thus keeping the injection spring 9 in a compressed state. The piston rod 7 is prevented from movement into the distal direction. At least the distal end 15*a* of the switching sleeve 15 is engaged or abuts with a proximal end 3*a* of the needle cover sleeve 3. The switching sleeve 15 is biased by a needle cover sleeve spring 10 into the distal direction. The distal end 10*a* of the needle cover sleeve spring 10 abuts a rim 15*b* on the switching sleeve 15 and the proximal end 10*b* of the needle cover sleeve spring 10 abuts a signaling element 11 and the signaling element abuts an end cap 12 that is axially and rotationally secured to the housing 2. In the initial state of the autoinjector 20, the force of the needle cover sleeve spring 10 in the proximal direction is guided to the end cap 12 of the housing 2 via the signaling element 11. In the distal direction, the needle cover sleeve spring 10 biases the needle cover sleeve 3 into the distal direction via the switching sleeve 15. For starting the injection, the needle cover sleeve 3 is pushed against the skin of the patient and moved in the proximal direction with respect to the housing 2 thereby moving the switching module 15, 8 in the proximal direction and tensioning the needle cover sleeve spring 10. In the most proximal position of the switching module 15, 8, the locking sleeve 8 may be axially engaged with the mechanic holder 5 (or alternatively to the signaling element 11 as will be discussed below) whereas the switching sleeve 15, axially guided and splined onto the locking sleeve 8, is kept by the needle cover sleeve 3 in the proximal position against the bias of the spring force provided by the needle cover sleeve spring 10.

The proximal movement of the switching module 8, 15 releases the engagement between the protrusions 6*c* on the holding element 6 and the recesses 7*a* in the piston rod 7. The spring force is released and the piston rod 7 moves into the distal direction whereas the holding element 6 can move an initial hub in the proximal direction until the proximal end 6*d* of the holding element 6 abuts the end cap 12 of the housing 2. Optionally, an acoustic or tactile signal is generated upon abutment indicating the start of the injection. The piston rod 7 abuts a stopper or piston head 19 in the prefilled syringe which is moved distally towards the outlet thereby expelling medicament through the needle 23.

The needle cover sleeve spring 10 is a metal coil spring acting as a compression spring and the proximal end 10*b* abuts the signaling element 11 which abuts the end cap 12 of the housing 2 before injection. The signaling element 11 includes two longitudinally extending arms 11*b* each having a protrusion 11*a* oriented towards the longitudinal axis L. The protrusions 11*a* engage another recesses 7*b* in the piston rod 7 and the sleeves of the switching module 8, 15 ensure that the signaling element 11 is axially coupled to the piston rod 7 before and during the initial stage of the injection. The arms 11*b* with protrusions 11*a* are also confined within the locking sleeve 8 thereby preventing release of the protrusions from the recesses. During the initial stage of the injection, the piston rod 7 is advanced distally and thereby also drives the signaling element 11 in the distal direction away from the end cap 12 through the locking sleeve 8. The signaling element 11 is moved in the distal direction by a distance or tensioning hub until the protrusions 11*a* are released from the recesses 7*b* in the piston rod 7 as the arms 11*b* are not confined by the locking sleeve 8 anymore and can flex radially outward. The arms 11*b* have another protrusion 11*c* that is directed in the radial outward direction and those outward protrusions 11*c* engage the switching module 8, 15 keeping the tensioning hub of the signaling element 11. The arms 11*c* may engage the locking sleeve 8 thereby keeping the locking sleeve 8 in the proximal position (alternatively the locking sleeve engages the mechanic holder 5 as discussed above). The arms 11*b* can slide along the outer surface of the piston rod 7 and at the end of the injection, the piston rod has advanced such that the arms 11*b* of the signaling element 11 can flex radially inward again and the signaling element 11 is released from the switching module 8, 15. The signaling element 11 is biased proximally by the needle cover sleeve spring 10 and is accelerated and moved back towards the end cap 12 thereby producing an audible and/or tactile end-of-injection click.

After the medicament has been delivered, the autoinjector 20 is removed from the skin and the switching sleeve 15 together with the needle cover sleeve 3 are forwarded by the needle cover sleeve spring 10 that is at least partially decompressed. The switching sleeve 15 moves in the distal direction and is sliding along the locking sleeve 8 which has been locked before injection to the mechanic holder 5. The switching sleeve 15 may be locked in the most distal position by a flexible arm 8*a* of the locking sleeve 8 engaging a cut out 15*c* of the switching sleeve 15 thereby preventing proximal movement of the switching sleeve 15 after injection. The needle cover sleeve 3 may be locked in the most distal position by arms 1*a* of the syringe holder 1 that radially extend into recesses 3*b* of the needle cover sleeve 3 thereby preventing proximal movement of the needle cover sleeve 3 after injection.

The end cap 12 is axially and rotationally fixed to the housing 2. The end cap 12 may be snap fitted, adhesively connected or welded to the housing 2. The end cap 12 can be the closure cap for the autoinjector delimiting the mechanical components of the device in the proximal direction if there are no further modules added to the autoinjector. The end cap may provide protrusions, ribs or 3D structures acting as shock absorbers. The end cap 12 may provide a platform or adapter for adding an additional module to the autoinjector. This may be an electronic module 16 and the module is closed by a closure cap 17 engaging the end cap 12 and/or housing 2 of the autoinjector. The closure cap 17 may provide protrusions, ribs or 3D structures on the outer surface acting as shock absorbers. In some cases, the module is a releasable module that can be released and separated from the autoinjector after injection. The electronic module 16 may include a sensor or switch 16*a* and a battery 16*b* and a printed circuit board 16*c*. The printed circuit board 16*c* may include a microprocessor, a transmitter/receiver unit, an antenna and/or a light source such as a LED. The light source may be used to signal the status of the device to the user, for example "ready to use" or "injection completed". The sensor 16*a* may be part of the PCB 16*c* as well and is configured to detect if the signaling element 11 is in the most proximal position. The sensor 16*a* may be a switch located on the PCB 16*c* detecting whether the signaling element 11 is in its most proximal position before injection and/or the most proximal position after injection and/or the absence of contact to the sensor during an injection. The signaling element 11 may have a protrusion extending into the proximal direction and optionally guided through a passage in the end cap 12 for contacting the sensor 16*a*. Alternatively, the signaling element 11 indirectly contacts the sensor 16*a*, for example via a pivoting element, a rotating element or an element that moves along the pen axis 18 that is part of or coupled to the end cap 12. The microprocessor detects the signals from the sensor 16*a* and is capable to transmit the data (for example time, duration, failure) of an injection to an external device using a communication module including, for example a transmitter and/or receiver.

The signaling element 11 or an extension of the signaling element 11 may therefore contact the sensor 16*a* directly or indirectly before an injection as the signaling element is in the most proximal position. During the injection the signaling element is driven by the piston rod 7 in the distal direction and the signaling element 11 or an extension therefrom may not contact the sensor 16*a*. At the end of the injection, the signaling element 11 moves in the proximal direction and may contact the sensor 16*b* again. Each event may be recorded and may be transmitted to an external device or may trigger a visual or acoustic signal by the electronic module.

Figure 3B:
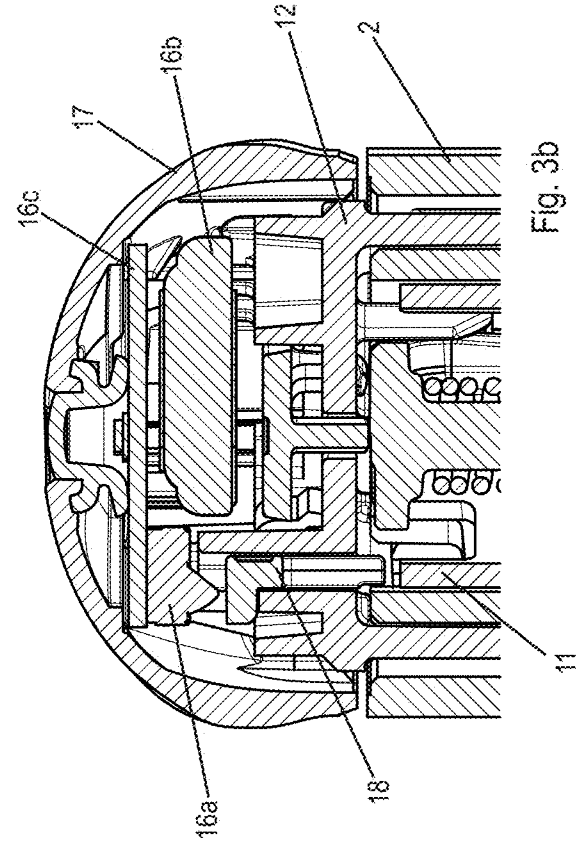
Fig. 3b Prior Art
FIG. 3*b*: The electronic module according to the prior art of FIG. 3*a*; autoinjector during use.
Figure 3A:
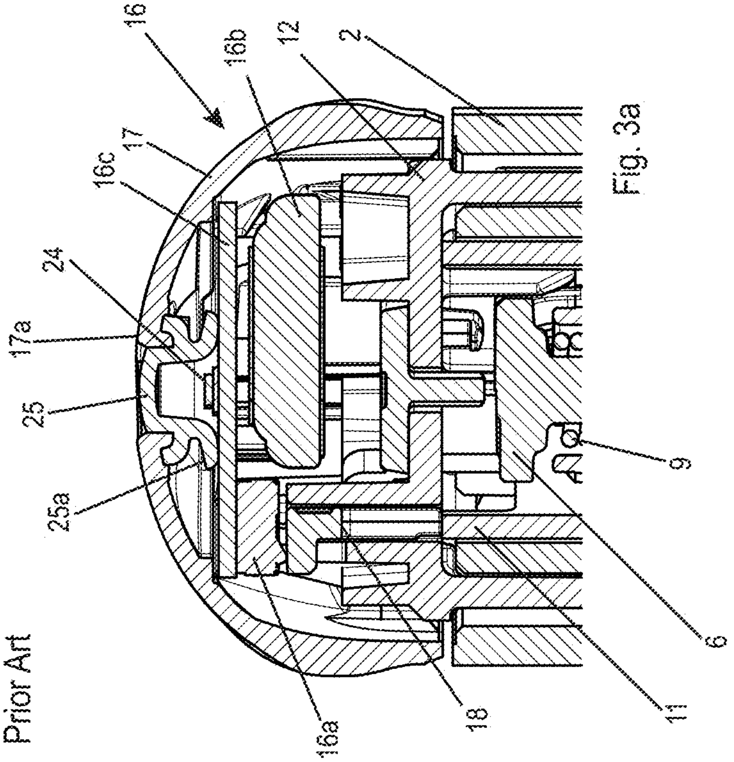

FIGS. 3*a* and 3*b* illustrate detail of the electronic module 16 according to the prior art and includes a separate switch 16*a* on printed circuit board 16*c*. The electronic module is located between end cap 12 and closure cap 17. The electronic module includes the battery 16*b* that is connected to the PCB. The closure cap 17 includes an aperture 17*a* that is closed by a transparent plug 25 such that an LED light source 24 on the PCB can provide optical signals to the user. The plug 25 may include elastic arms 25*a* surrounding a bore in the plug for guiding the LED light. The elastic arms 25*a* may also provide a resilient force on the surface of the PCB for mechanically fixing the PCB or for compensating manufacturing tolerances. The electronic module 16 is attached to the proximal end of the auto injector by a mechanical interface, for example by a bayonet type of connection between the closure cap 17 and the housing 2 or between the closure cap 17 and the end cap 12. The housing 2 encloses the injection mechanism driven by injection spring 9 that may act on the signaling element 11 and/or the holding element 6 during different stages of the injection. In the embodiment presented in FIGS. 3*a* and 3*b*, the signaling element 11 is configured to abut the distal end of detection pin 18 (FIG. 3*a*). During an injection, the signaling element 11 moves in the distal direction and actuates the switch 16*a* (FIG. 3*b*). The detection pin in this embodiment moves along the longitudinal axis of the autoinjector but may also tilt or pivot with respect to the longitudinal axis L. The actuation of switch 16*a* may register the start of the injection or the end of the injection or trigger the start of a holding time after the injection. The electronic module, according to the prior art presented in FIGS. 3*a* and 3*b*, includes a separate switch 16*a* located on the PCB which occupies space, additionally a separate detection pin is used that is part of, and enclosed in the autoinjector.

Figure 4B:
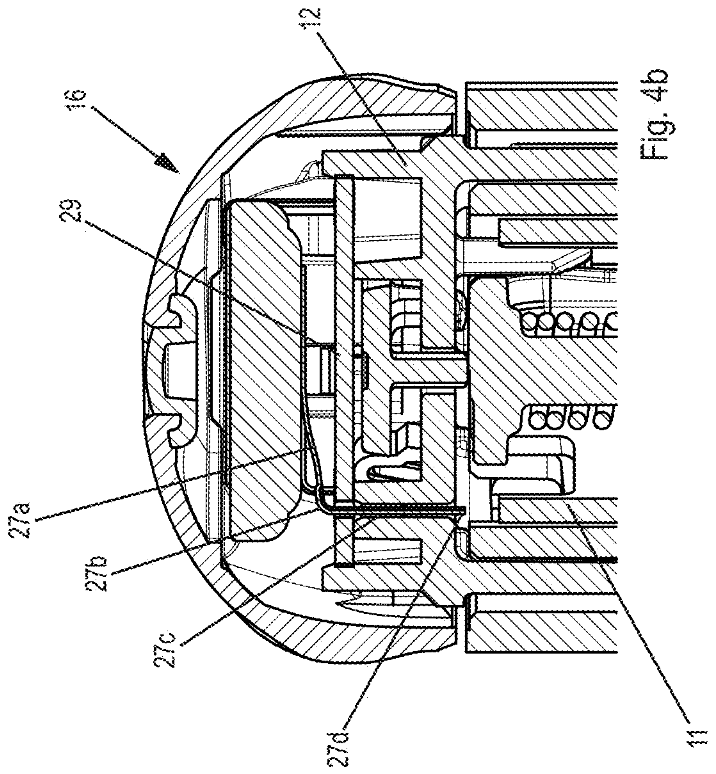
FIG. 4*b*: The electronic module of FIG. 4*a*; autoinjector during use, according to the present disclosure.
Figure 4A:
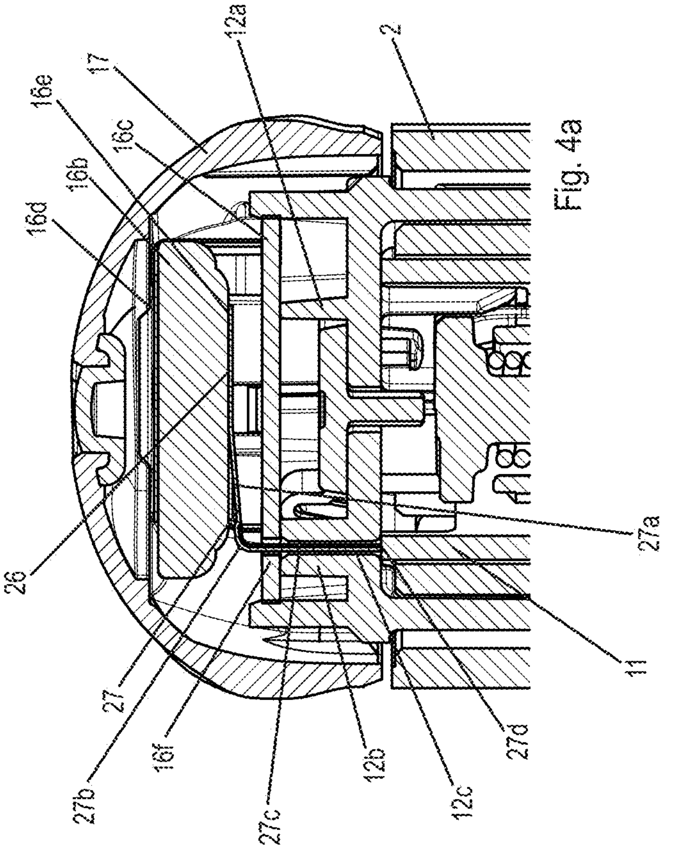
FIG. 4*a*: Longitudinal cross-section of an electronic module according to an embodiment of the present disclosure; autoinjector before use.

FIG. 4*a* presents an electronic module according to embodiments of the present disclosure. The electronic module is enclosed in the closure cap 17 which is attached to the housing 2 or to the end cap 12 of an autoinjector. The PCB 16*c* is positioned on extension 12*a* and the proximal end of a guide sleeve 12*b*. The battery 16*b* is fixed to the PCB by battery holders 26 contacting the terminals 16*d*, 16*e* of the battery 16*b*. One of the battery holders 26, in this example the battery holder contacting the negative terminal 16*e*, includes a battery contact extension 27. The battery contact extension 27 and the battery holder 26 for the negative terminal are made as one unitary component from a stamped sheet of metal. The battery contact extension 27 includes a part that is oriented essentially parallel to the battery terminals and a part that is oriented about or essentially perpendicular to the battery terminal. A bend or kink 27*b* is positioned between the parallel and perpendicular oriented parts. The part of the battery contact extension oriented perpendicular to the battery terminal provides for a detection pin 27*c* and the part parallel to the terminals provides for a leaf spring 27*a*. The PCB includes a passage 16*f* for the detection pin 27*c*. The distal end 27*d* of the detection pin 27*c* is guided by the guide sleeve 12*b* through a passage 12*c* in the end cap 12 towards the signaling element 11 of the autoinjector. Before use of the autoinjector, the signaling element 11 abuts the distal end 27*d* of the detection pin and pushes the detection pin 27*c* against the bias provided by the leaf spring 27*a* in the proximal direction thereby creating a switching gap between the battery contact extension 27 and the PCB 16*c* to open the switch discussed in more detail below.

The electronic module of FIG. 4*a* is presented in FIG. 4*b* during use of the autoinjector. The signaling element 11 is driven in the distal direction by the injection spring during dose delivery. The distal end 27*d* of the detection pin 27*c* follows the distal movement due to the bias provided by the leaf spring 27*a*. The battery contact extension 27 contacts a contact that is part of an electronic circuit 29 located on the PCB 16*c* thereby closing the switch.

A comparison of FIG. 3*a* and FIG. 4*a* shows the effect of replacing the switch 16*a* according to the prior art by the battery contact extension 27 and the electric activation contact 28 of the present disclosure. Fewer parts are thus required for activating the module by actuating switch according to the present disclosure. Additionally, the space occupied by the switch 16*a* in FIG. 3*a* is available for a larger battery having a greater capacity in FIG. 4*a* according to the present disclosure.

Figure 5B:
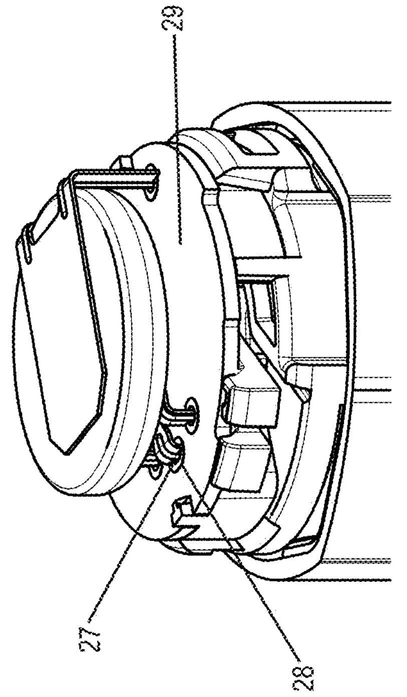
FIG. 5*b*: An isometric view of the electronic module, autoinjector during use, according to the present disclosure.
Figure 5A:
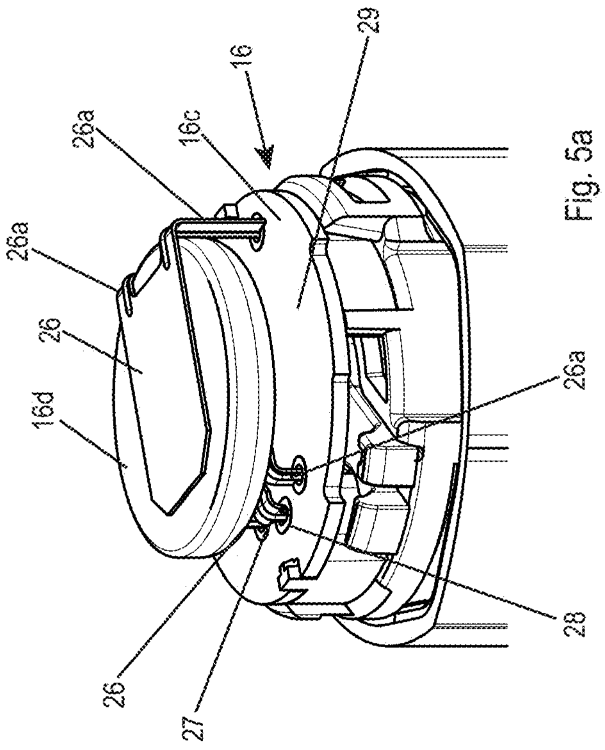
FIG. 5*a*: An isometric view of the electronic module; autoinjector before use, according to the present disclosure.

An isometric view of the electronic module 16 according to embodiments of the present disclosure without the closure cap is presented in FIG. 5*a*. The battery holder 26 contacts the positive terminal 16*d* (top surface of the battery) and extensions 26*a* are connected to the PCB 16*c* providing for mechanical support to the battery holder 26 and/or for the electric activation contact to the electronic circuit 29 on the PCB. Extensions 26*a* also extend from the battery holder contacting the negative terminal (bottom surface of the battery). In the embodiment presented in FIG. 5*a*, two extensions 26*a* extend from the battery holders 26 to provide mechanical support for the battery and/or electric contacts to the electronic circuit 29 on the PCB. The battery contact extension 27 is located between the two extensions 26*a* for the battery holder contacting the negative terminal or bottom surface of the battery. The autoinjector is shown in FIG. 5*a* before use and the battery contact extension 27 is moved in the proximal direction against the bias of the leaf spring such that the battery contact extension 27 is not contacting the electric activation contact 28 that is part of the electronic circuit 29, e.g., the switch (27, 28) is open. The autoinjector is shown in FIG. 5*b* during use and the switch (27, 28) is closed, according to embodiments of the present disclosure.

Figure 6B:
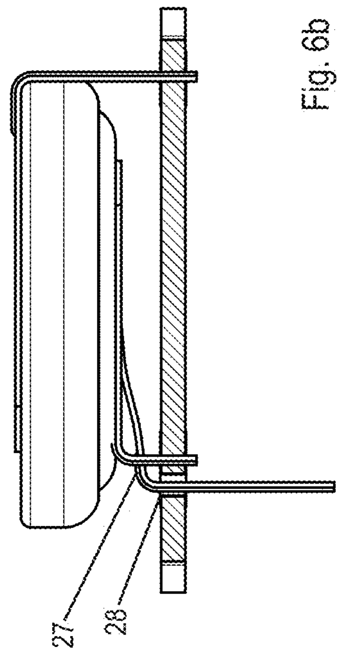
FIG. 6*b*: Side view of the electronic module, switch closed, according to the present disclosure.
Figure 6A:
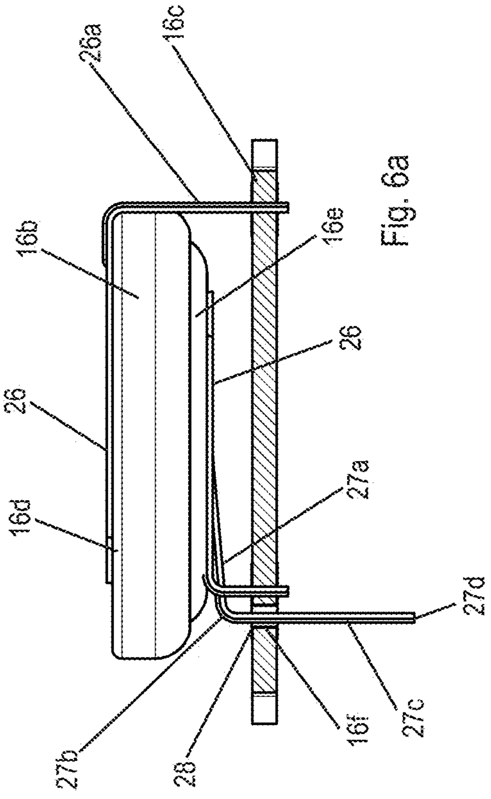
FIG. 6*a*: Side view of the electronic module, switch open, according to the present disclosure.

A side view of the electronic module with an open switch is presented in FIG. 6*a* and with a closed switch in FIG. 6*b*, according to embodiments of the present disclosure. The two battery holders 26 with their extensions 26*a* position, and hold the battery 16*b* on top of the PCB 16*c*. The battery contact extension 27 extends from the negative battery terminal 16*e*. The kink 27*b* of the battery contact extension is located between the leaf spring 27*a* and the detection pin 27*c*. The PCB 16*c* includes the passage 16*f* for the detection pin 27*c* and the distal end 27*d* is configured for engaging the drive element of the autoinjector thereby pushing the battery contact extension 27 in the proximal direction against the bias of the leaf spring. The battery contact extension 27 does not contact the electric activation contact 28 in FIG. 6*a* (switch open) and the switch is closed in FIG. 6*b*.

Figure 7B:
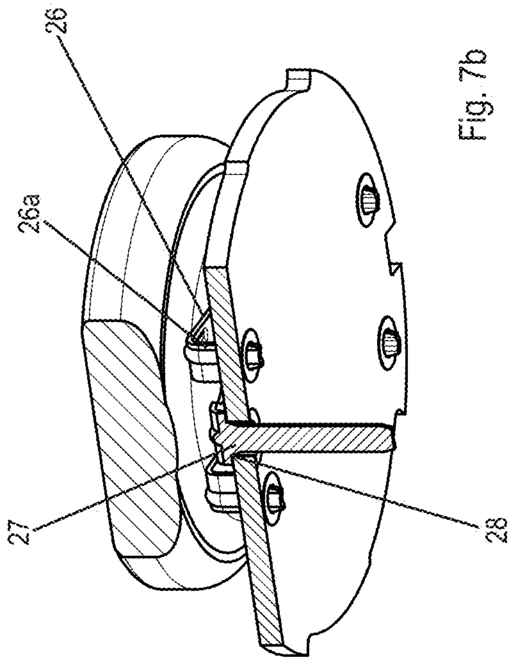
FIG. 7*b*: An isometric view of an electronic module with a tapered section for the battery contact extension; switch is closed, according to the present disclosure.
Figure 8B:
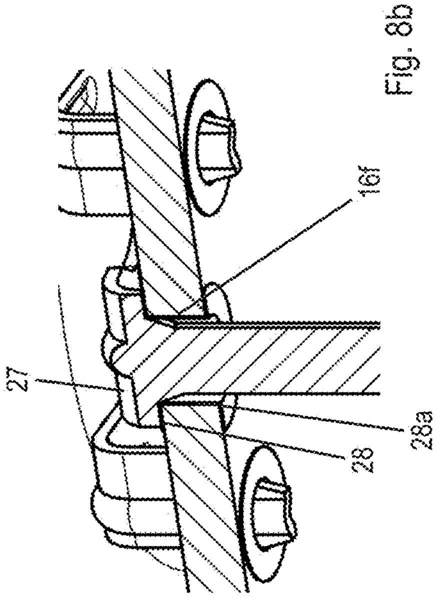
FIG. 8*b*: Detail of FIG. 7*b* according to the present disclosure.
Figure 7A:
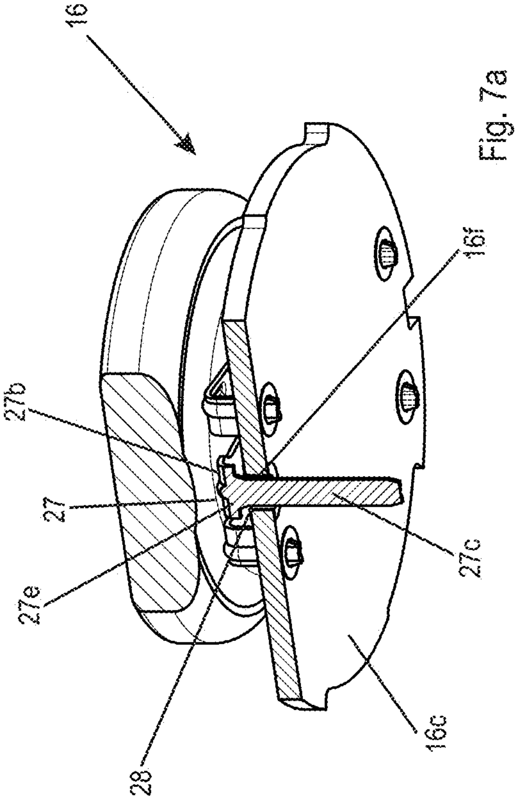
FIG. 7*a*: An isometric view of an electronic module with a tapered section for the battery contact extension; switch is open, according to the present disclosure.
Figure 8A:
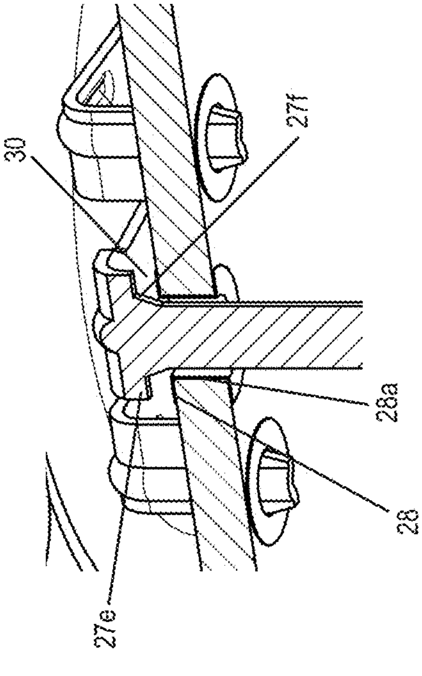
FIG. 8*a*: Detail of FIG. 7*a*, according to the present disclosure.

Isometric bottom views of the electronic module, according to embodiments of the present disclosure, with cross-sectional cuts are shown in FIGS. 7*a* and 7*b* and details shown in FIGS. 8*a* and 8*b* respectively. The battery contact extension 27 is made from a stamped metal sheet with the detection pin 27*c* formed as a narrowed extension that is adjacent to the kink 27*b* thereby leaving a lateral extension 27*e* on one side of the passage 16*f* in the PCB as the detection pin 27*c* is guided through the passage 16*f*. A tapered section 27*f* depends from the lateral extension 27*e* (detail shown in FIG. 8*a*). The electric activation contact 28 on the PCB surrounds the passage 16*f* and may contact the lateral extension 27*e* of the battery contact extension 27 for closing the switch 27, 28. The switch is open in FIGS. 7*a* and 8*a* as there is a switching gap 30 between the battery contact extension 27 and the electric activation contact 28. The switch is closed in FIGS. 7*b* and 8*b* and the lateral extension 27*e* of the battery contact extension 27 contact the electric activation contact 28. As an option, the electric activation contact may cover at least a part of the surface of the passage 16*f* itself. The electric activation contact in the passage 28*a* is configured for contacting the tapered section 27*f*. The tapered section may remove deposition or corrosion products from the surface of contacts 28, 28*a* when moving from an open switch (FIG. 8*a*) to a closed switch (FIG. 8*b*).

Embodiments of the present disclosure have been presented for the purpose of illustration and description. They are not intended to be exhaustive or to limiting. Obvious modifications or variations are possible in light of the above teachings. The embodiments were chosen and described to provide the best illustration of the principles of the implementations and the practical applications thereof, and to enable one of ordinary skill in the art to utilize the invention in various embodiments and with various modifications as are suited to the particular use contemplated.

PART ANNOTATION

1 Syringe holder
1*a* Arms
2 Housing
3 Needle cover sleeve
3*a* Proximal end
3*b* Recess
4 Pen cap
5 Mechanic holder
5*c* Holding spring
6 Holding element
6*a* Central pin, guide pin
6*b* Arms
6*c* Protrusion
6*d* Proximal end
7 Piston rod
7*a* Recess
7*b* Recess
8 Locking sleeve
8*a* Flexible arm
9 Injection spring
9*a* Distal end
9*b* Proximal end
10 Needle cover sleeve spring
10*a* Distal end
10*b* Proximal end
11 Signaling element
11*a* Protrusion
11*b* Arms
11*c* Protrusion
12 End cap
12*a* Protrusion/rim
12*b* Guide sleeve
12*c* Passage end cap
14 Needle shield remover
15 Switching sleeve
15*a* Distal end
15*b* Rim
15*c* Cut out

16 Electronic module
16*a* Prior art sensor/switch
16*b* Battery
16*c* Printed circuit board, PCB
16*d* Battery terminal (+)
16*e* Battery terminal (−)
16*f* Passage PCB
17 Closure cap
17*a* Aperture
18 Pivoting element, detection pin
19 Stopper or piston head (Bung)
20 Auto injector or medicament delivery device
21 Prefilled syringe
21*a* Proximal end
22 Needle shield
23 Hollow needle
24 LED
25 Transparent plug
25*a* Wings
26 Battery holder
26*a* Extension
27 Battery contact extension
27*a* Leaf spring
27*b* Kink
27*c* Detection pin
27*d* Distal end
27*e* Lateral extension
27*f* Tapered section
28 Electric activation contact PCB
28*a* Electric activation contact passage
29 Electronic circuit PCB
30 Switching gap or physical or air gap
L Longitudinal axis
8, 15 Switching module
27, 28 Switch

What is claimed is:

1. A medicament delivery device comprising an electronic module, the module comprising:

a printed circuit board comprising an electronic circuit;

a battery; and a switch element configured for activating the electronic module, wherein the switch element comprises an electric activation contact configured for providing a connection with the electronic circuit and a battery contact extension extending from a terminal of the battery, wherein the battery contact extension is biased towards the electric activation contact and configured for closing an air gap between the battery contact extension and the electric activation contact, wherein the battery contact extension is configured to engage an actuation element of the medicament delivery device, the actuation element configured to push against the biased battery contact extension to thereby maintain the switch element open, wherein the battery contact extension comprises a spring element configured for biasing the battery contact extension towards the electric activation contact, and wherein the battery contact extension comprises a detection pin, and wherein the spring element is located between the terminal of the battery and the detection pin.

2. The medicament delivery device according to claim 1, wherein the detection pin is adapted to abut the actuation element in a direction along a longitudinal axis of the medicament delivery device.

3. The medicament delivery device according to claim 2, wherein the detection pin and the spring element are provided as a unitary component made from an electrically conductive material.

4. The medicament delivery device according to claim 3, wherein the spring element is a leaf spring, and wherein the detection pin is oriented about perpendicular to the leaf spring forming a kink between the leaf spring and the detection pin.

5. The medicament delivery device according to claim 4, wherein the electric activation contact at least partially surrounds a passage in the printed circuit board.

6. The medicament delivery device according to claim 5, wherein the detection pin at least partially passes through the passage, and a distal end of the detection pin is configured to engage the actuation element of the medicament delivery device.

7. The medicament delivery device according to claim 6, wherein the electric activation contact at least partially covers an inner surface of the passage.

8. The medicament delivery device according to claim 7, wherein the battery contact extension comprises a lateral extension and a tapered section for contacting the electric activation contact, and wherein the lateral extension has an outer dimension greater than an inner dimension of the passage.

9. The medicament delivery device according to claim 2, wherein the electric activation contact at least partially surrounds a passage in the printed circuit board.

10. The medicament delivery device according to claim 9, wherein the detection pin at least partially passes through the passage, and a distal end of the detection pin is configured to engage the actuation element of the medicament delivery device.

11. The medicament delivery device according to claim 10, wherein the electric activation contact at least partially covers an inner surface of the passage.

12. The medicament delivery device according to claim 11, wherein the battery contact extension comprises a lateral extension and a tapered section for contacting the electric activation contact, and wherein the lateral extension has an outer dimension greater than an inner dimension of the passage.

13. The medicament delivery device according to claim 1, wherein the engagement between the actuation element and the battery contact extension is adapted to be released and to close the air gap upon movement of the actuation element of the medicament delivery device axially along, or tilting with respect to, or rotating around a longitudinal axis of the medicament delivery device when the medicament delivery device is being used.

14. The medicament delivery device according to claim 1, further comprising a mechanical interface configured for releasable attachment of the electronic module to the medicament delivery device.

15. The medicament delivery device according to claim 14, wherein the detection pin is part of or located in the mechanical interface.

16. The medicament delivery device according to claim 1, wherein the electronic module is adapted to be released from the medicament delivery device only after the device has been used.

17. The medicament delivery device according to claim 1, wherein the medicament delivery device is a spring driven auto injector, and wherein an injection spring is configured to move a drive element in a distal direction during medicament delivery and rotates the actuation element or tilts the actuation element or axially moves the actuation element in the distal direction to release the engagement between the battery contact extension and the actuation element.

* * * * *